United States Patent
Cochran

[19]

[11] Patent Number: 6,048,846
[45] Date of Patent: Apr. 11, 2000

[54] COMPOSITIONS USED IN HUMAN TREATMENT

[76] Inventor: Timothy M. Cochran, P.O. Box 9060, Cedar Pines Park, Calif. 92322

[21] Appl. No.: 09/031,227

[22] Filed: Feb. 26, 1998

[51] Int. Cl.[7] .......................... A61K 31/595; A61K 9/48
[52] U.S. Cl. .................. 514/168; 514/171; 514/570; 424/195.1; 424/423; 424/430; 424/434; 424/443; 424/451; 424/464
[58] Field of Search ..................... 514/168, 171, 514/570; 424/195.1, 423, 430, 434, 443, 451, 464

[56] References Cited

U.S. PATENT DOCUMENTS 5,536,506  7/1996  Majeed et al. .................. 424/464
5,883,086  3/1999  Craft ............................... 514/168

*Primary Examiner*—F. T. Moezie
*Attorney, Agent, or Firm*—Colin P. Abrahams

[57] ABSTRACT

A composition for treatment of a human body comprises a combination of at least one hormone, at least one amino acid, at least one enzyme and/or vitamin, and least one mineral. The relative proportions of the hormone, amino acid, enzyme and mineral in the combination are balanced with respect to each other so as to be present in effective amounts to substantially restore to optimal levels in the body the hormone, amino acid, enzyme and mineral The hormone, amino acid, enzyme and mineral in the combination further operate synergistically to provide both nutrients and command components to enable the body to effectively utilize the nutrients. The invention is also a method of forming a composition for the treatment of a human body.

34 Claims, 9 Drawing Sheets

FIGURE 1

| Type | Morning | Noon | Evening |
|---|---|---|---|
| Pregnenolone | | 50mg | 50mg |
| DHEA | 25 mg | 50mg | 50mg |
| Melatonin | | | 5 mg (taken 2 hours before your bedtime) |
| Coenzyme Q-10 | 120mg | 120mg | 120mg |
| Anthocyanidin | 300mg | 300mg | 300mg |
| Proanthocyanidin | 200mg | 200mg | 200mg |
| Garlic:10,000mcg Allicin | 400mg | 400mg | 400mg |
| Beta Carotene | 18mg | 18mg | 18mg *1 capsule Multi-Carotene & Lipoic |
| Alpha Carotene | 11mg | 11mg | 11mg |
| Gamma Carotene | 1mg | 1mg | 1mg |
| Lycopene | 1mg | 1mg | 1mg |
| Lutien | 3mg | 3mg | 3mg |
| Zeaxanthin/ Astaxanthin | 130mcg | 130mcg | 130mcg |
| Vitamin E (Alpha & Gamma Tocopheryl) | 800IU | 800IU | 800IU |
| Vitamin C | 1000mg | 1000mg | 1000mg |
| Niacin (Inositol Hexanicotinate) | 400mg | 400mg | 400mg (wait unitl you lower hypertension medication for a couple weeks) |
| Folic Acid | 400mcg | 400mcg | 400mcg |
| Vitamin B-1 (Thiamine Monoitrate) | 50mg | 50mg | 50mg |
| Vitmin B-2 (Riboflavin) | 50mg | 550mg | 50mg |
| Vitmin B-3 (Niacinamide) | 50mg | 50mg | 50mg |
| Vitamin B-5 (Calcium Pantothenate) | 100mg | 100mg | 100mg |
| Vitamin B-6(Pyidoxine Hydrochloride) | 50mg | 50mg | 50mg |
| Vitamin B-12 (Cyanocobaiamin) | 50mcg | 50mcg | 50mcg |
| Biotin | 300mcg | 300mcg | 300mcg |
| Inositol | 50mg | 50mg | 50mg |
| Choline | 50mg | 50mg | 50mg |
| PABA | 50mg | 50mg | 50mg |
| Vitamin D-3 (Cholecalciferol) | 400IU *1 capsule 1 time per day | | |
| Calcium (Gluconate) | 1000mg | 1000mg | 1000mg |
| Magnesium | 400mg | 400mg | 400mg |
| Phosphorus | 350mg | 350mg | 350mg |
| Iodine (Potassium Iodide) | This group is in the basic RDA capsule. Take 1 capsule morning and 1 in the evening | | |
| Iron (Terrous Fumerate) | (Plus others, but you can read the label) | | |

FIGURE 1 CONTINUED

| | | | |
|---|---|---|---|
| Manganese | 2.5mg | | |
| Potassium Gluconate | 450mg | 450mg | 450mg |
| Copper | | 2mg *1 capsule once per day | |
| Zinc (Gluconate) | | 30mg | |
| Lecithin | 1200mg | 1200mg | 1200mg |
| Chromium Picolinate | 600mcg | 600mcg | 600mcg |
| Selenium | 100mcg | 100mcg | 100mcg |

Amino Acids: required group (1 Amino Acid multi caps x 3 times per day)

| | | | |
|---|---|---|---|
| L-Alanine | 60mg | 60mg | 60mg |
| L-Arginine | 1554mg | 1554mg | 1554mg (3-500mg caps x 3 times per day) |
| L-Aspartic Acid | 107mg | 107mg | 107mg |
| Bromelain | 50mg | 50mg | 50mg |
| L-Cystine | 23mg | 23mg | 23mg |
| L-Glutamine | 1185mg | 1185mg | 1185mg (2-500mg caps x 3 times per day) |
| Glycine | 48mg | 48mg | 48mg |
| L-Histidine | 41mg | 41mg | 41mg |
| L-Isoleucine | 71mg | 71mg | 71mg |
| L-Leucine | 97mg | 97mg | 97mg |
| L-Lysine | 77mg | 77mg | 77mg |
| L-Methionine | 55mg | 55mg | 55mg |
| Pancreatin 4X | 25mg | 25mg | 25mg |
| Papain NF | 50mg | 50mg | 50mg |
| L-Phenlalanine | 88mg | 88mg | 88mg |
| L-Poline | 82mg | 82mg | 82mg |
| L-Serine | 71mg | 71mg | 71mg |
| L-Threonine | 59mg | 59mg | 59mg |
| L-Tyrosine | 603mg | 603mg | 603mg (1-500mg caps x 3 times per day) |
| Taurine | 1,990mg | 1,990mg | 1,990mg (3-500mg caps x 3 times pe day) |
| L-Valine | 97mg | 97mg | 97mg |
| N-Acetyl-L-Cysteine | 1000mg | 1000mg | 1000mg |
| L-Carnitine | 500mg | 500mg | 500mg |
| Piperine | 10mg | 10mg | 10mg |
| EPA (Eicosapentaenoic Acid) | 1000mg | 1000mg | 1000mg |
| GLA (Gamma-Linolenic Acid | 1000mg | 1000mg | 1000mg |
| Omega-3/Omega-6 Fatyy Acid | 1000mg | 1000mg | 1000mg (Flax Seed Oil Extract) |
| Lipoic Acid | 50mg | 50mg | 50mg (2-25mg caps x 3 times per day) |

COMPOSITIONS USED IN HUMAN TREATMENT

FIELD AND BACKGROUND OF THE INVENTION

This invention relates to composition combinations for the treatment of the human body to both maintain the health of the body and fight disease therein.

More particularly, the invention relates to various compositions, including, but not limited to, hormones, vitamins, enzymes, amino acids, minerals and other substances found naturally in the body, and combining them in various forms and dosages according to the nature of the condition being treated such that the combination, when administered to a person, restores and/or creates optimal biochemical levels of the compositions within the body.

It is a well-known fact that, as humans age, there is both a cellular and molecular tissue degeneration. This may be due to the natural aging process, as well as various forms of disease which have invaded the body. As the body ages, its biochemical capacity to fight disease on a molecular level declines. Disease and tissue degeneration gradually destroy the health of the person, ultimately resulting in death.

The present invention addresses this situation by attempting to alter the body chemistry from that which has allowed the body to create a medium in which the disease has developed. Many diseases do not exist or do not develop in young adults in their twenties, whereas older people in and beyond their sixties will much more readily support the same disease.

The present invention is therefore a composition comprised of various components and substances which modulate the physiological conditions within the body. The invention is based on the proposition that altering and correcting the biochemical plane changes the physiological medium that allowed a disease to exist may effectively reduce or obviate the disease. The combination of components which constitute the composition of the present invention are therefore designed to fight the causes of the disease, and not simply to mask their effect.

The invention is a composition, a method of treatment using the composition, and a method for formulating the composition designed to treat the disease at the molecular/cellular level, focusing strongly on DNA and RNA regulation, RNA template protection, protection of genes and chromosomes, and enhancement of the molecular/cellular language which is spoken and understood by the cells of the body. The invention uses, amongst others, specific and calculated quantities of hormones, amino acids, amino sugars, coenzymes, enzymes and mineral ions in an effort to fight disease and restore the conditions of the body on a cellular level.

SUMMARY OF THE INVENTION

According to one aspect of the invention there is provided a composition for treatment of a human body, the composition comprising a combination of: a) at least one hormone; b) at least one amino acid; c) at least one enzyme and/or vitamin; d) at least one mineral wherein the relative proportions of said hormone, amino acid, enzyme and mineral in the combination are balanced with respect to each other so as to be present in effective amounts to substantially restore to optimal levels in the body the hormone, amino acid, enzyme and mineral, the hormone, amino acid, enzyme and mineral in the combination further operating synergistically to provide both nutrients and command components to enable the body to effectively utilize the nutrients.

According to another aspect of the invention there is provided a method of forming a composition for the treatment of a human body, the method comprising: providing in combination: (a) at least one hormone; (b) at least one amino acid; (c) at least one enzyme and/or vitamin; (d) at least one mineral; adjusting the relative amounts of the hormone, amino acid, enzyme and mineral in the combination to be balanced with respect to each other and present in effective amounts to substantially restore to optimal levels in the body the hormone, amino acid, enzyme and mineral, the hormone, amino acid, enzyme and mineral in the combination operating synergistically to provide both nutrients and command components to enable the body to effectively utilize the nutrients.

In one aspect of the invention, there is provided a composition for treating diseases and cellular degeneration by modulating the chemistry of the body on a wide ranging comprehensive level. By this is meant that the combination of components which constitute the composition address biochemical deficiencies in the body usually resulting from disease or the aging process. The composition endeavors to restore to the extent possible a wide range of biochemical levels of important substances produced and required by the body and therefore alter the environment in which disease within the body has been allowed to develop.

Depending on the nature of the condition to be treated, different combinations of substances and the doses thereof may be used to formulate a regimen to address biochemical deficiencies and restore a "biochemical platform level" to prevent an environment in which disease can thrive. The present invention is particularly effective in treating such conditions as cardiovascular diseases, auto-immune diseases, Parkinson's disease and the like. The composition has been shown to work repeatedly, especially in the treatment of cardiovascular disease. The tables and data based on actual patient response to the composition of the invention clearly indicate the positive effect on the body by comprehensive augmentation of essential and critical biochemical substances.

The composition of the invention is based on a predetermined combining of hormones, amino acids, enzymes and minerals. Based on the condition of the patient, at least these four components are combined in a composition and ingested so as to provide nutrients as well as command components to enhance DNA and RNA regulation, such regulation being sufficient to, at the least, produce tissue regeneration. "Command components" refers to those components of the composition which regulate, instruct, manipulate, assist in cell communication, protect against deterioration, control or otherwise generally have a function aside from nutrient requirements. Such components may, however, also have in addition a nutrient function.

Hormones are the products of living cells and function so as to produce a specific effect on the activity of cells remote from the point of manufacture of the hormone. Hormones are secreted into the body fluids by a cell or a group of cells, profoundly affecting and controlling the behavior of other cells within the body.

Amino acids are essential compounds used by the body in the synthesis of proteins. Amino acids may be synthesized by living cells within the body, or are obtained by the body as essential components of the diet. Not all amino acids can be synthesized by the body. For example, ten amino acids are mandatory and necessary for life, but are not produced by the body and must therefore be obtained nutritionally on a daily basis. These amino acids are arginine, histidine, isoleucine, leucine, lysine, methionine, phenylalanine, threonine, tryptophan and valine. In addition to the above, there are a number of non-essential amino acids, the importance of which may be significantly increased in times of sickness, stress, disease and as the body ages.

Enzymes are fairly complex proteins that chemically help in the transformation of one substance into another inside the cell and function as catalysts in specific biochemical reactions. The enzymes are thus catalytic substances, usually protein, and upon obtaining access to and entering a human cell, either initiate or increase the efficiency rates of chemical reactions within the cell. These enzymes alter and may increase metabolism rates within the cell, including anabolism, the constructive metabolism concerned with the synthesis of macro-molecular structure, and catabolism, the metabolism resulting in breakdown of complex materials often with the release of energy.

Vitamins are generally included in the enzyme category due to their enzyme-like results and effects on molecular/cellular structure. Generally, the vitamins will cause an increase in the rate of chemical inter-reaction within the body.

Mineral ingestion in acceptable ratios is essential to the proper functioning of the human body. If the relative ratios of mineral ions within the body falls out of balance, the normal function of the body on a cellular level will be greatly impaired. There are many required minerals controlling in or assisting in a wide range of cellular operations. Some of the most important of these minerals include: iron, calcium, potassium, magnesium, manganese, copper, zinc, iodine, selenium and the like.

The various components of the composition may be introduced in quantities and dosages which take into account the patient condition, age, extent of disease, body chemistry, blood levels and other relevant factors. Discussed in detail further below in this application are specific components, and their importance and possible doses for use within the composition are set out. It has been found that, using the above formula and based on results of cardiovascular medical trials, significant cell regeneration is possible.

Determining the composition in making up the treatment composition is based on the accepted understanding that the function of the human body is a combination of biochemical interreactions, all forming a complex arrangement whereby these reactions effect and act out upon one another. By introducing certain components into the body and thereby attempting to control the biochemical contact between the cells, the "cellular dialogue" can be advantageously changed and modulated. To the extent that the cellular dialogue or conversation can be controlled, for example at the RNA template, the ability exists to change the course or direction of the organism's function at the molecular level. Further, conditions can be changed to emulate those during an earlier biological time period of the patient, and appropriate doses of the various components which make up the composition administered to offset cellular retardation. The body's biochemical output production may typically drop 10–12% every 4 years on average, and the ability to introduce various chemical components into the body in predetermined combinations and dosages addresses and may reverse this retardation. In effect, therefore, the composition of the invention to some extent produces a cellular genesis with the ability to stop and correct tissue degeneration and/or oxidation. By strengthening cellular instructions and maintaining optimal relative proportions and/or levels of a large number of biochemical components, the overall biochemical system may be strengthened and enhanced to regain its ability to fight disease from an earlier time period. By "optimal relative proportions" and "optimal levels" is meant the individual's relative amounts of a wide range of components which were present during the physiological prime of the body, usually between 18 and 25 years of age.

Further, the so-called "biochemical medium" of the body may be corrected and enhanced to reduce or eliminate conditions where disease can first take hold.

BRIEF DESCRIPTION OF THE DRAWINGS

FIG. 1 is a table showing a specific regimen administered to a patient;

DETAILED DESCRIPTION OF THE PREFERRED EMBODIMENTS

Figure 2:
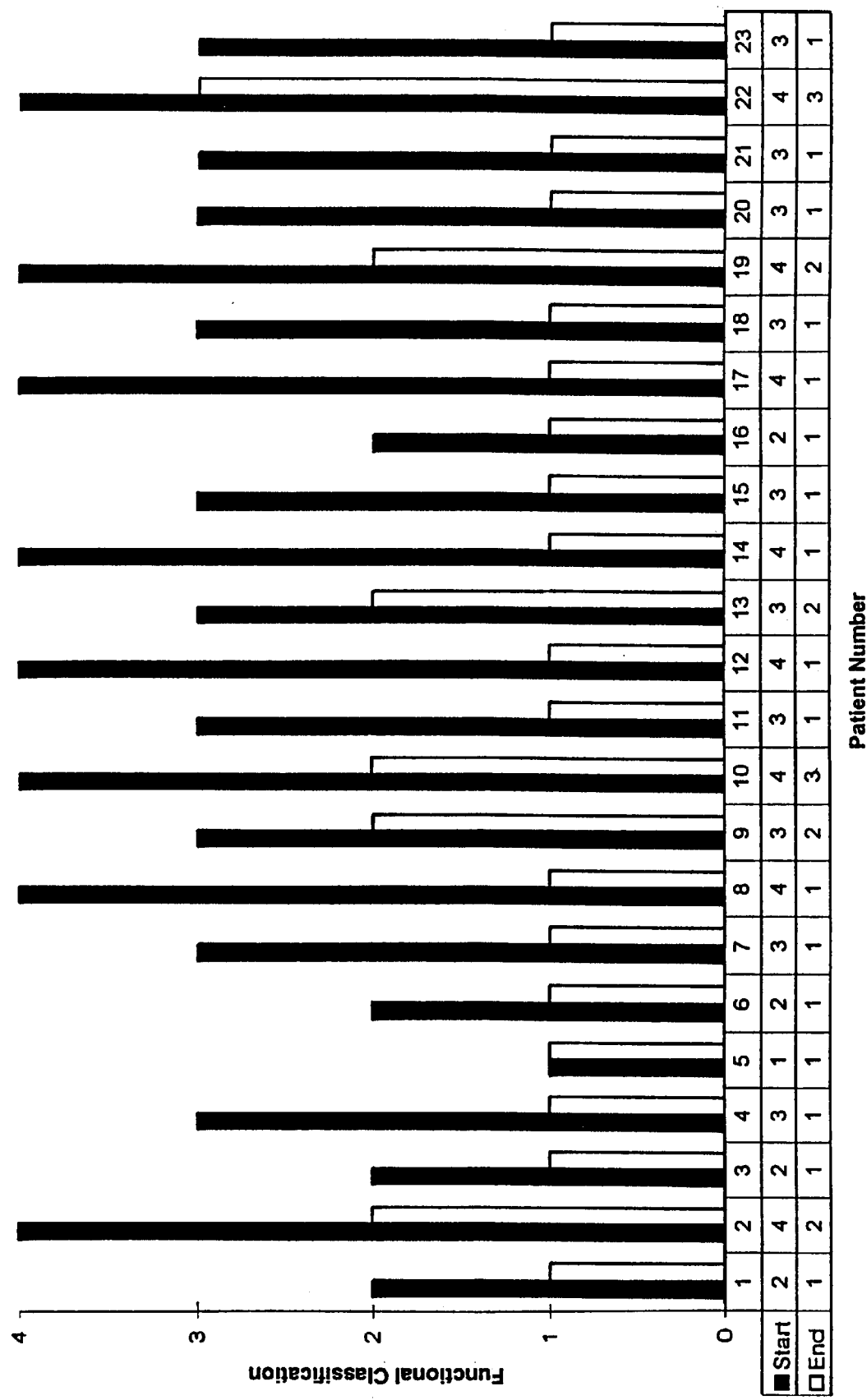
FIG. 2 is a diagram showing start and end NYHA levels for selected patients.

In one aspect, therefore, the invention comprises a composition of nutrient and biochemical components for the treatment of the human body, the composition comprising one or more of the following: a hormone, amino acid, enzyme and minerals.

Preferably, the hormone is at least one or both of dehydroepiandrosterone (DHEA) and melatonin. Vitamin D3 may be used as prohormone.

"Enzymes" is intended as an umbrella term and preferably includes enzymes, coenzymes, vitamins and antioxidants. More specifically, the enzyme may comprise coenzyme Q-10. The antioxidants preferably include multi-carotenes alpha, beta and gamma-carotenes, lycopene, lutein and xeanthin. The enzymes are also intended to include vitamins, including Vitamin B, Vitamin B complex, Vitamin C, Vitamin D (other than D3) and Vitamin E.

The minerals may include a wide variety of compounds used by the body, including, but not limited to: calcium, magnesium, phosphorus, iodine, iron (ferrous fumarate), manganese, potassium, copper, zinc, chromium and selenium.

When the components are administered as a group in combination, and constitute a complete regimen of treatment, the body's physiology may be modulated to emulate its physiology at a much younger age. The preferred age range to emulate is 18 to 25 years.

In the first six months of private clinical trials for patients on the regimen of the present invention, the average NYHA level improved from 3.1 on average to 1.3 on average. This was accompanied by improvements in cardiovascular function. Additionally, patients' blood pressures dropped from 153.7/113 to 101.5/69.6, and the average pulse rate dropped from 104 to 76. Blood chemistries improved significantly. On average, patients' total blood cholesterol levels dropped 39.6 mg/dl. LDL-cholesterol levels dropped 48.3 mg/dl, and HDL-cholesterol levels increased by 14.5 mg/dl. On average, patients' HDL/LDL cholesterol ratios improved by 216%, and triglycerides dropped 29.3 mg/dl. Prior to the regimen of the present invention, conventional medications were not able to bring about significant improvements.

The regimen constituting the biochemical formula of the present invention may involve supernutritional amounts of nutrients and "mega" amounts of several hormones. The goal of the regimen is to restore levels of certain "super hormones" to those of healthy 20–25 year olds.

Success in areas outside of cardiovascular disease has been achieved. For example, in preliminary treatment of Parkinson's disease, symptoms diminished within 24 hours, and, in one particular instance, within 48 to 72 hours of treatment of the regimen, no symptoms were noticeable. Pilot studies on Lupus and Fibromyalgia syndrome, chronic fatigue syndrome and rheumatoid arthritis have also shown promising results. This application also describes treatment of arthritis and the success in the treatment thereof.

As mentioned above, the regimen or biochemical formula of the invention involves the use of quantities of nutrients and hormones in higher range "supernutritional" levels. Many of the dosages described in this application are designed for persons with sometimes advanced diseases. The regimen prescribes very high doses of hormones, amino acids, enzymes, and minerals which are maintained in a balance. In this regard, it is pointed out that adding only some nutrients does not achieve the objective. The regimen attempts to overwhelm the disease, and attack it from as many different biochemical pathways and direct avenues of approach as possible to destroy it before it can kill the patient. In attacking the disease, the use of hormones and chemical messengers tell the cells what to do. Vitamins, minerals, amino acids, enzymes, coenzymes and essential fatty acids are prescribed so as to attack the disease from every biochemical pathway, 24 hours a day. A very hostile environment is provided so that the disease has difficulty surviving.

The dosages prescribed take into account the amount of deterioration that has occurred in the patient. Deterioration of a person, on a biochemical or cellular level, commences past the age of 22 to 25 years. Hormonal production drops, absorbency rates inside the intestines are dropping and large amounts of toxins, such as alcohol, may be ingested. The body gets less nutrients, less amino acids, enzymes and other important nutrients crossing over the intestinal tract into the bloodstream. Thus, the peculiarities of the individual are taken into account in establishing the dose level.

In establishing the doses, the treatment approach is different from the conventional medical approach, which asks "what is there causing cardiovascular disease?". The regimen is based on the question "what is not there now (for example at 62 years of age) that allow the causes of cardiovascular disease to develop?". In other words, the approach is to determine what is missing in the body that was present in earlier years, and studying these biochemical levels in a person's prime as compared to what is being produced and ingested by the body at later times.

The other approach of the invention is to determine the driving force in the body. The DNA/genes and chromosomes are, in a sense, immortal, having come down through the ages and continue to live in the body in one form or another. Levels of hormones produced in the body at earlier ages are never duplicated at a later time, and either turn off or deteriorate in later years. Thus, controlling and emulating the molecular operation enabling a person to reach the age of 20–25 years is of prime interest. Understanding this language involves controlling and regulating DNA.

All cells obey the laws of physics and chemistry, so by manipulating the DNA, instructions are provided in a language so that tissues are able to regenerate accordingly. Thus, providing an all encompassing nutrient approach, the DNA is able to function and produce the necessary substances that maintain the body in a healthy state at an earlier age.

The invention looks at cell communication and biophysics. Looking at the disease and its causes, it is noted that a massive amount of correlated total bioenergy enabled the body to reach its biological prime. Massive amounts of very complex biochemical actions, reactions, interactions and pathways start at one point and then proceed to complete physical development. Thereafter, deterioration sets in, resulting in not only a biochemistry problem, but in a biophysics and physics problem. From conception through birth, childhood, puberty, adolescence, and early adulthood, a huge correlation of hormones, amino acids and enzymes push and develop the body. After early adulthood, this flattens out on a biochemical plateau and then reduction sets in. With this reduction or contraction, free radical damage, a toxic environment and other factors contribute to the deterioration. At this point, a combination of biophysics and biochemistry must be considered to address the problem on a molecular level. The lack of the biochemical instructions and resources, along with toxin ingestion and a host of other problems, cause the system to break down.

There is no point in feeding the body the necessary nutrients without providing it with the instructions on how to use them. Thus, prescribing one "supervitamin" or another is ineffective, since it takes all vitamins and other substances to ensure tissue maintenance, regulation and metabolism. Aging results in the reduction in cellular efficiency and capacity rate, and intestinal absorbency rates drop resulting in the body receiving less and less incoming nutrients. For example, a body at one time is accustomed to providing, for example, 400–450 mcg/100 ml of DHEA blood level in a mature male approximately 22 years old. In patients with cardiovascular problems, 0–25 mcg/100 ml of DHEA is found in the blood. DHEA is simply not there anymore in the necessary quantities.

The regimen not only feeds the cell what it needs, but attempts to supply instruction for the use thereof. Thus, a body may be able to absorb some of the nutrients but will not be able to use them to maximum capacity if, for example, the mitochondria of the cells are not working properly. It would be ineffective to give a cell overwhelming amounts of nutrients without giving it the proper directions, from the amounts of hormones and amino acids, necessary to stimulate them to use the nutrients properly.

Hormones

DHEA is one of the most abundant hormones in humans and mammals and is an essential component in many physiological functions. It has been found that DHEA is deficient in persons suffering from major diseases including obesity, diabetes, high blood pressure, cancer and others. DHEA is manufactured in the body from cholesterol. While DHEA levels often decline with age, cholesterol levels have been found to increase with age. (see "DHEA: The Youth and Health Hormone", C. Norman Shealy, M. D.; 1996 Keats Publishing Inc.).

In administering DHEA and determining appropriate levels thereof, the DHEA levels in the patient at between 20 and 25 years of age are used as a yardstick. In many instances, the target amount of DHEA is 450 mg/ml of blood for males and 380 mg/ml of blood for females. A variation of 5% from these levels would be optimal, although variations up to about 15%–20% may be acceptable. Since these are the blood levels of DHEA of the normal male and female in the 22–25 year old age bracket, the dosage of DHEA used in the biochemical formula of the invention is calculated so as to augment DHEA levels in the body to these amounts.

The amount of DHEA to be administered to reach this level will obviously vary according to the age and condition of the patient. For example, a 60 year old male patient approximately 5 feet 10 inches in height and 180 pounds in weight will typically require 100–125 mg of DHEA on a daily basis. Preferably, this dosage would be administered three times a day to spread the intake of the DHEA over a 24 hour period. As mentioned above, the amount of DHEA produced by the body (in the adrenal glands) decreases with age. Studies appear to indicate that there is a 2.5% decreasing ratio in this hormonal production rate each year.

In determining the amount of DHEA to be administered, other characteristics and attributes of the patient would also be considered. For example, patient ingestion of alcohol, tobacco, caffeine and drugs may cause rapid degeneration and destruction of body tissues, and the extent and duration of such ingestion will assist in determining the quantities of DHEA to be administered.

In general, DHEA doses are preferably between 75–200 mg per day, varied according to the age and condition of the patient. Females would usually require about 20% less than males. Target doses may be prorated to take into account a 2.5% decline per year in the amount of DHEA produced from the age of about 25 years in males and 22 years in females. While doses up to 200 mg per day have been used in clinical trials for very old patients (70 to 80 years or older), doses over 200 mg per day have not been used. Higher doses would typically be for older patients of large physical size and stature.

Melatonin is another hormone which is produced naturally by the body, secreted by the pineal gland in the brain. Melatonin has versatile and varied effects, and recent clinical studies have shown its ability to improve immune functions, reduce or prevent heart disease, lower cholesterol, as well as slow down the aging process. Melatonin is also known for its powerful antioxidant characteristics. Various antioxidants, as well as their beneficial effects on the body, are discussed below, but in general terms, an antioxidant assists in stemming the damaging effects of the free radical chain-reaction in the body, which may damage cell membranes, cell bodies and chromosomal material.

Melatonin is preferably administered in doses ranging between 5 mg and 12 mg per day. However, doses may start lower than this, and may be 3 mg per day or less. The patient is preferably, over a period of time, administered increasing doses of melatonin, preferably up to between 5 mg and 8 mg per day. Additionally, the regimen of the present invention is such that the melatonin is taken only once a day, at dusk local time, since optimal results have been noted when melatonin is taken at this time. The regimen requires that melatonin be administered to duplicate normal ratios of about 10:1, but variation in this ratio is possible. Indeed, some patients obtain positive responses and healthy results when the ratio is adjusted to a different ratio +/−25% of the original target ratio.

Optimal effects and advantages are obtained when the doses of the various components which form the regimen of the invention are fairly evenly divided and taken in three separate medications over the course of the day. The doses may be taken at the conventional times, namely, morning, noon and at evening or dusk. There are, however, certain exceptions to this general approach, particularly with respect to the melatonin dosage discussed above, which is optimally taken only at dusk.

Enzymes

Coenzyme Q-10, also known as ubiquinone, is commonly found in humans and is utilized in the human body for its energy properties. It is to be noted here that there are a variety of molecular formulations ranging from Coenzyme Q-6 to Coenzyme Q-10, although only the Coenzyme Q-10 is found in humans. However, animal forms of this coenzyme can be converted to Q-10 when ingested as part of the diet. Therefore, while this patent application typically refers to the administering of Coenzyme Q-10, it is within the scope of the invention to use other formulations of this coenzyme.

Enzymes usually consist of two portions, namely a protein portion otherwise known as an apoenzyme, and a cofactor portion. The apoenzyme is constituted by a string of amino acids which find their basis in the chromosomal material. The other non-protein portion or co-factor portion of the enzyme is often called a coenzyme.

Coenzyme Q-10 plays a significant role in the Krebs or citric acid cycle resulting in the production of an energy-rich compound called adenosine triphosphate, abbreviated as ATP. The energy contained within the compound ATP is dispensed to and used by the body to carry out normal functions. When dispensing the energy, ATP releases a phosphate group, and approximately 7,000 calories of energy, and is converted to adenine diphosphate, or ADP. The ADP, in turn, upon receiving energy from food and nutrients in the body, is once more converted to ATP, thus forming the energy cycle and constituting the generator or power base of the body.

The main site of ATP production is in the mitochondria of the cell. Administering doses of the various components constituting the regimen of the invention have an immediate effect at the cellular level, transmitting instructions to the mitochondria within the cells. These mitochondria are double-membraned organelles of the cell cytoplasm that process cellular energy by the oxidation of substrates, and store it in the form of ATP, as discussed above. The metabolism of the cell depends on a constant supply of incoming "raw materials" available for continual use. Furthermore, the cycle requires the removal of finished substances and the waste products of these interactions by the circulation of the blood. In this way, each cell operates as a small power plant, with three stages of energy production operations. These are: provision of raw materials, manufacture of the energy by using the raw materials in converting ADP to ATP, and the disposal and discharge of the waste by-products. The entire operation is controlled by the cell nucleus and maintained by the available energy reserves.

Coenzyme Q-10 is a critical component in the creation of cellular energy within the cell, and it has a direct effect and enhances the activity of the mitochondria within the cell. The highest concentrations of Coenzyme Q-10 can be found in the heart, while lesser amounts are found in other organs such as the liver, brain, lungs etc. The daily dosage of the Coenzyme Q-10 preferably varies between 240 mg and 600 mg. A preferred middle range is between 360 mg and 540 mg. Once more, the amount of the dosage will depend on the particular condition of the patient, and since Coenzyme Q-10 is a critical component in the treatment of cardiovascular disease, the extent of development of the cardiovascular disease within the patient, the condition of the heart, and the "NYHA" (New York Heart Association) level of the patient will all be taken into account. This is in addition to the normal parameters such as the height, weight and age of the patient, in determining the optimal dosage for administration.

Antioxidants

Generally, antioxidants are compounds that sacrifice themselves to oxygen. Antioxidant compounds have chemistries that allow them to react readily with oxygen. The ease of this reaction enables antioxidant compounds to react with the free radical generators, and quench free radical production. A free radical is an incomplete highly reactive molecule capable of destroying an enzyme, protein, genetic material or even an entire cell over time. Additionally, the free radical usually generates a chain of free radical reactions resulting in thousands of free radicals being released to destroy the cell components. This process is called biological magnification. The antioxidants not only help protect the body against the destructive effects of these free radicals, but also stimulate the immune response to help fight existing disease, and they tend to normalize the balance of hormone-like chemicals in the body. ("The Antioxidants—The Nutrients that Guard Your Body" by Richard A. Passwater, Ph. D., 1985, Keats Publishing Inc.).

The antioxidants therefore protect and repair cellular tissue from this free radical damage. Some important antioxidants are, but not limited to, the following: multi-carotenes, beta-carotenes, alpha-carotenes, gamma-carotenes, lycopene, lutein and zeanthins. Further antioxidants include Vitamin E, Vitamin C and Niacin. The use of these antioxidants helps to preserve not only the chromosomal genetic material against breakdown, but also proteins, enzymes and other substances within the body. Since destruction or damage of chromosomal material within the cell has a direct impact on the future ability of that cell to produce functional and effective proteins and enzymes, the need to protect the body from the free radicals is an important one.

The composition of the present invention preferably includes multi- and single-carotenes. Preferably, 50–60 mg of beta-carotene per day, 25–40 mg of alpha-carotene per day, 1–5 mg of gamma-carotene per day, 1–5 mg of lycopene per day, 1–10 mg of lutein per day and 200–500 mcg of zeaxanthin/astaxanthan per day are administered. Depending on the body characteristics and condition of the patient, these amounts may vary by 30%–40%.

With respect to the carotenes, the clinical results show that they function most effectively when used together in a united effort. Research has shown that by supplementing with just one of the carotenoids, such as beta-carotene, levels of other carotenes in the body may actually be reduced. Alpha-carotene has been found to be more effective than beta-carotene for free radical attacks on the cells, and promoting cellular health on the molecular level. Further, alpha-carotene remains in the carotene form almost twice as long as beta-carotene, so that the antioxidant properties thereof work for a longer period of time inside the body.

Lycopene is an extremely efficient carotenoid which is significantly more effective than others. Lycopene appears to be almost twice as effective as the beta-carotene and one hundred times better than and/or stronger than Vitamin E at fighting free radicals and the damage that they cause. The mixture of the carotenoids, generally as indicated above, plus the use of lycopene, increases the cellular resistance and maintains and supports proper tissue health. These are a highly effective combination of antioxidants, having the effect of first increasing and then maintaining overall cellular health tissue.

The regimen may also include alpha-, beta- and gamma-Vitamin E, preferably given in doses of 800–4,000 IU per day. More normal ranges may preferably fall between 2,000 and 3,000 IU per day, depending on patient characteristics. The regimen further includes Vitamin C, with daily dosage ranges between 1,500 mg and 4,000 mg. Once more, a more normal range will preferably fall between 2,000 and 3,000 mg.

The various dosages of the carotenes, Vitamin E and Vitamin C mentioned above are typically given three times per day, morning, noon and evening, in substantially equal dosages.

Vitamin B3, or niacin, is one of the more stable B vitamins, and is the common name for two compounds, namely, nicotinic acid and nicotinamide. Niacin is an important component in the biochemical formula of the invention in that it plays many diverse and critical roles in the cells of the body, both supplying energy and maintaining the integrity of the body cells. Although niacin is synthesized in the liver of the body, from the amino acid tryptophan, the body's demand and need for niacin is strong, and increases with age. The use of niacin is important particularly in the treatment of cardiovascular diseases. The normal body requires a healthy balance of HDL and LDL cholesterol, since this is essential for cardiovascular health and function. The niacin dosage within the biochemical formula helps to control the body's production of VLDLs (or very low density lipoproteins) which are proteins used by the body to create LDLs. The LDLs are bad for the body, and constitute the destructive cholesterol molecule.

Typically, the form of niacin used may produce a flushing, redness or rash to the skin when consumed in large doses. This has been found to be due to the biochemical reaction produced by such niacins and resulting in the sudden release of prostaglandins. The present invention has been able to use these larger doses, but with no side-effects, by using niacin which contains inositol hexanicotinate. Inositol is molecularly bonded to niacin, and in conjunction therewith serves to slow the absorption of nicotinic acid. This effectively eliminates or substantially reduces the flushing or rash in the skin of patients. In this way, effective amounts of niacin inositol hexanicotinate can be administered without the adverse skin side effect, to reduce the LDL levels, stabilize HDL levels and lower, overall, cholesterol and triglyceride levels.

In the biochemical formula of the invention, preferably about 400 mg to 1,600 mg per day of niacin inositol hexanicotinate is administered, with the preferred range being between 800 mg–1,200 mg per day. As with most of the other components of the composition, the niacin inositol hexanicotinate is administered three times a day, morning, noon and night, in approximately equal doses.

The composition of the present invention preferably includes a Vitamin B complex, which preferably, but not necessarily, comprises all of the following components: folic acid, Vitamin B1, Vitamin B2, Vitamin B3 (niacin), Vitamin B3 (niacinamide), Vitamin B5, Vitamin B6, Vitamin B12, biotin, inositol, choline and para-amino benzoic acid (abbreviated PABA). The combination of the various components which constitute this Vitamin B complex is administered to provide all or most of the essential B-complex vitamins which are required resources for the operation of the nervous system and the adrenal glands.

Research has shown that the primary defense mechanism of the immune system against stress are products of the adrenal glands. These glands secrete hormones directly into the bloodstream. Each gland is divided into two parts, namely, an inner medulla and an outer cortex. The medulla section produces two types of hormones and takes all of its cellular instructions from the nervous system. The cortex produces and secretes the hormones called corticosteroids, which affect the way foods are stored, processed and used inside the body. The adrenal glands also have a direct linkage to healing mechanisms inside the body, and strengthen the response and function of the immune system. However, the complex vitamins are water soluble, and are quickly excreted from the body. Therefore, the regimen of the invention requires that the biochemical levels of these components of the Vitamin B complex be maintained in order to assist on an ongoing basis the fighting of the disease. This entails frequent administering of the vitamin B complex on a regular basis to replace those which are dissolved and excreted by the body.

The various individual B vitamins operate as discrete units to support nerve and brain tissue function, and also assist the body in coping with stress. As a group, they also complement each other and act as coenzymes involved in the cellular production of energy. When one of the essential B vitamins is not present, or is only present in low concentrations, the response of other pro-Vitamin Bs may also be reduced and weakened. Further, reduced concentration or absence of a particular B vitamin may cause an imbalance to occur when these B vitamins compete with each other for absorption into the intestine. The particular Vitamin B complex used in the regimen of this invention, the contents of which are set forth above, and the various doses of which are described below, are designed to be highly comprehensive, and are balanced to ensure maximum transfer and absorption into the intestines.

The Vitamin B complex advantageously is made up of the following components, each present in the proportions and dosages indicated:

| Component | Preferred Range (per day) | Approximate Normal Quantity (per day) |
|---|---|---|
| Folic Acid | 2400 mcg–4800 mcg | 3600 mcg |
| Vitamin B1 | 100 mg–200 mg | 150 mg |
| Vitamin B2 | 100 mg–200 mg | 150 mg |
| Vitamin B3 (niacin) | 10 mg–30 mg | 15 mg |
| Vitamin B3 (niacinamide) | 100 mg–300 mg | 150 mg |
| Vitamin B5 | 100 mg–400 mg | 300 mg |
| Vitamin B6 | 150 mg–350 mg | 225 mg |
| Vitamin B12 | 100 mcg–200 mcg | 150 mcg |
| Biotin | 600 mcg–1,200 mcg | 900 mcg |
| Inositol | 100 mg–200 mg | 150 mg |
| Choline | 100 mg–200 mg | 150 mg |
| PABA | 100 mg–200 mg | 150 mg |

The Vitamin B complex, when administered in effective doses and ratios with respect to each other, nourishes and supports the nerve and brain tissue facilitating proper mental function. Furthermore, the Vitamin B complex provides the correct support for proper metabolic function of the body's immune system, and helps the body effectively manage stress, fatigue and tension. Importantly, too, the Vitamin B complex provides a solid chemical base of support for a properly functioning cardiovascular system.

Folic acid is one of the components of the Vitamin B complex mentioned above. Folic acid has been found to enhance and support healthy cardiovascular function by helping the body get rid of the toxin homocysteine. Homocysteine (an amino acid) is produced naturally through digestion, but the aging process increases the quantities in which it is produced, which in turn has a direct effect on healthy cholesterol levels. It has been shown that folic acid supplementation is likely to bring down homocysteine levels, along with the risk of heart attack, stroke or other blood vessel problems.

Inositol also forms part of the Vitamin B complex described above, and produces a form of niacin which is safe in that it does not produce flushing or rashes. Inositol also supports cardiovascular health by helping the body to regulate cholesterol levels to lower levels found in the body during earlier years. Biotin assists and supports energy production inside the cell and helps convert the folic acid into its biologically active form. Choline, which is a constituent of acetylcholine, is a neuro transmitter that aids in the proper transmission of brain waves and therefore facilitates brain function. PABA, another component of the Vitamin B complex, assists the body in its use of pantothenic acid, which supports and enhances the formation of red blood cells and acts as a coenzyme in the breakdown and utilization of protein.

It will therefore be appreciated that the vitamin B complex addresses a multitude of the body's functions and biochemical components to restore the level of these components to former levels when the body was able to withstand and better fight many diseases. The regimen adopts an "across the board" approach in addressing multiple body biochemistries, all of which, when functioning properly, enhance and augment each other for the general well-being of the body.

Minerals

The composition of the invention also calls for the use of minerals and mineral ions, since the ingestion of these minerals, as well as maintaining proper ratios thereof within the human body, is a prerequisite to correct and normal functioning of the body at a cellular and tissue level.

Calcium and magnesium work together and cooperatively support a number of body functions. Together, they help support nerve transmission, and are also required in the regulation of energy levels. These minerals are also required to help and maintain heart function and have a direct effect on maintaining proper blood pressure levels. Calcium is needed to facilitate effective blood-clotting, and it has an enzymatic action. It is further used in neuromuscular excitation, and for maintenance and function of the cell membrane. Further, it is used in the activation of hormonal secretion.

Vitamin D facilitates the absorption of calcium through the intestines into the bloodstream. The calcium, as is well known, has a major role in supporting bone density and strength. Proper intakes of calcium assist in the prevention of osteoporosis, a problem related to age, and found particularly in cardiovascular patients. Women can lose up to 15% of total skeletal mass within 5 to 10 years following menopause, and it is also during this time period that cardiovascular disease may start to take hold and develop. Proper intake of calcium, alone and in the proper ratios with other components, may play a significant role in reducing or eliminating these problems.

The daily regimen of the invention preferably includes about 1500 mg–2500 mg of calcium, about 600 mg–1000 mg of magnesium, and about 600 IU–1000 IU of Vitamin D-3. Typically, a preferred dosage would be about 2000 mg of calcium, 800 mg of magnesium and 800 IU of Vitamin D-3, with variations and proportions being adjusted to conform to the particular condition and characteristics of the patient. Variations of 35% higher or lower than those doses set forth above would be appropriate depending on the patient.

The biochemical formula also requires RDA levels of iodine and iron (RDA=recommended daily allowance). Iodine and iron would normally be administered twice per day, namely, once in the morning and once in the evening, although any time during the 24 hour period would be acceptable.

Potassium gluconate is another mineral which will form part of the biochemical formula, and would preferably be dosed between 1,800 mg–5400 mg per day (300–900 mg of element potassium), with a variation of 20% each way depending upon the condition and particular characteristics of the patient.

Potassium is an extremely important component, and is an essential mineral for proper cardiovascular and neurological function. Potassium not only assists in the regulation of blood pressure throughout the cardiovascular system, but increases the efficiency of neurological firing of nerve transmission impulses when maintained at optimal levels. Proper quantities of potassium stabilize and lower the heart rhythm rate. Further, potassium plays an important role in biochemical reactions resulting in the secretion of hormone actuates.

Another important function of potassium is to decrease sodium levels in body tissue, on a cellular and a molecular level. While sodium is needed by the body, excess amounts thereof may cause cellular tissue destruction. The potassium ion molecule has the ability to enter the cell and lock onto the sodium ion making its removal possible. The potassium then "escorts" the sodium from the cells throughout the bloodstream, storing it in the liver for further removal. There it is processed into bile salts and passed into the large intestine where it is excreted from the body.

By using potassium to remove sodium, kidney function is also improved. While the hormone aldosterone helps regulate the amount of sodium inside the body at any given time, the aging process results in the reduced production of this hormone and, therefore, sodium is not as readily removed from the kidneys at a more advanced age (such as 65 years or older) as it was at 25 years. Therefore, the regimen of the present invention uses potassium particularly on older patients for this purpose.

Controlling sodium levels in this regimen by the use of potassium, also lowers blood pressure. While it is a routine practice of medical doctors to advise lower salt intake to reduce high blood pressure, the present invention attempts to address and give assistance to the problem of higher sodium by restoring and balancing levels of potassium.

In this invention, typical potassium doses may be preferably between 75 mg–200 mg or more three times per day. In certain instances, 1,000 mg–1,200 mg or more of potassium per day may be ingested to maintain the balance referred to above. The doses are preferably spread out during the day in order to reach and maintain the optimal effect.

A preferred aspect of the present invention is the administering of potassium when bonded or chelated with an amino acid or a simple sugar. For example, potassium gluconate, as shown in clinical trials, has better absorbability and assimilation into the bloodstream.

The inventor has noticed other advantageous effects in the use of potassium. Proper levels of potassium assist in the lowering of cholesterol levels, and also help reverse or slow down the loss of protein in the urine (proteinuria). This is believed to be the result of the interaction in the kidneys flowing from the proper ratios of potassium, sodium and several hormones, including aldosterone.

Possible signs of potassium deficiency include a loss of feeling, numbness or a tingling sensation in the feet, legs, arms or hands, and the ingestion of potassium to appropriate levels may address this problem. Further, muscular weakness, fatigue or lethargy, another age-related health problem, can be improved with the use of potassium. Improvement in the transmission of nerve messages and the enhancement of the muscular tissue itself are some of the important results of increased levels of potassium.

Doses of potassium in excess of 1,000 mg spread out through the day, divided in equal doses, are not highly recommended unless improvements are not maintained in which case much higher doses can be used. Less potassium is absorbed by older or aged patients, with the absorbability rate being from 60%–85% less than in a person of 22 years of age. In younger persons, potassium intake is generally through the small intestinal wall, and the amount of absorption greatly decreases with age. This may be one of the reasons why older patients tend to suffer from cardiovascular and circulatory problems.

Another advantage of potassium is its effect when forming a biochemical interface with anti-diuretic hormones (also called vasopressin) and norepinephrine. These hormones, produced by the pituitary gland, have a direct reaction on the kidneys to increase the reabsorption of water. Potassium causes a counter-balancing of the effects of these pituitary hormones, and is most important for the functioning of the normal kidney, in order to correct the amount of discharge of toxins, and maintain proper blood pressure levels.

Zinc is found in all cells in the body, and is an integral component of over 200 enzymes. Zinc is highly concentrated in red and white blood cells and contributes to the proper functioning of a number of hormones. For example, zinc has been shown to affect the hormone dihydrotesterone (DHT) which, at elevated levels, has been linked to prostrate gland enlargement. Zinc's role in supporting and maintaining proper levels of this hormone is significant since research indicates that more than 50% of all men between ages 40 and 60 have elevated DHT levels.

Moreover, zinc is abundant in the bone, kidneys, liver, pancreas and the retina. It plays a major role in supporting the immune system, interacts in the antioxidant metabolism, and is involved in the metabolism of energy on the cellular level, as well as the synthesis of DNA and RNA in the cell nucleus.

In administering zinc, it is often advantageous to link it with an amino acid, and a mixture of zinc with arginate, histidinate and gluconate (preferably in proportions of about 50%, 25% and 25% respectively) enhances its effect. Zinc may be given in doses of 90 mg per day. However, doses in excess of about 120 mg per day of chelated zinc can adversely impact LDL levels, which could increase.

The biochemical formula of the invention also calls for the inclusion of Vitamin K, and 600 mcg–1,200 mcg may be the normal range, with a preferred amount being approximately 900 mcg, again depending on the condition and characteristics of the patient.

Copper, also preferably linked to an amino acid, for example 50% gluconate and 50% lycinate, may be used, and may be administered with the zinc. Up to 6 mg of copper may be the normal dosage, with variations between 20% and 35% each way.

Advantageously, the composition of the invention includes lecithin and/or lecithin choline. Lecithin is a natural source of choline, a substance required for transmission of information between nerve cells. It has been found that approximately 19 g of lecithin provides approximately 27 mcg of choline. 3600 mg–7200 mg of lecithin choline is administered daily. Approximately 25%–50%, preferably about 35% of this dose comprises phosphatidylcholine, which has about three times the concentration of choline. Lecithin is important in the maintenance of cell membranes, keeping them from hardening and preventing damage caused by oxidation. The fatty protective sheaths that surround the nerves in the brain and muscle cells all contain large amounts of lecithin.

Lecithin provides the body with a form of choline known as phosphatydal choline. This choline is normally made by the liver, but natural levels decrease with age. Therefore, supplementing choline is most important in order to restore the chemical levels in the body to physical prime levels at about 20 to 25 years of age.

Choline has important functions within the body. For example, the choline in lecithin acts as a lipotropic agent, ensuring proper transport and metabolism in fats. Further, choline is needed to make acetylcholine, a neurotransmitter in the brain, adequate amounts of which are critical for optimal nerve activity and normal mental and memory functions. Lecithin is also high in phosphorus, and combines with iron, iodine and calcium, the importance of which have already been described above in enhancing and supporting brain function.

Chromium is an essential trace mineral, and plays a vital role in sensitizing the body's tissue to the hormone insulin. In turn, insulin maintains the normal nutritional metabolism of protein/carbohydrate. Chromium is preferably administered in chelation with picolinic acid to form chromium picolinate. It regulates the metabolism of proteins, fats and especially carbohydrates and helps return cholesterol levels to healthy/normal levels. Chromium piconolate would normally be administered at between 1,200 mcg and 2,000 mcg per day. A typical range would preferably fall between 1,400 mcg and 1,800 mcg. A preferred administration would be 3 doses, morning, noon and evening, of about 400–600 mcg each.

The composition may include selenium and piperine, preferably as a mixture, and advantageously with a ratio of selenium:piperlne at 10:1. While other ratios may also be appropriate, tests to date have found the 10:1 ratio to be an effective one. The mixture, in typical form, may therefore comprise about 300 mcg–600 mcg selenium and 45–100 mcg Piperine per day, spread morning, noon and night. Some patients, due to their physical condition, would be more effectively dosed at 400 mcg selenium to 40 mcg piperine. Variations of up to 25% or more may be appropriate, again depending on the condition of the patient. Doses as high as 600 mcg selenium and 60 mcg piperine have been used in trials for certain patients, but as soon as the patient reaches the threshold of improvement, doses are lowered in order to return them to normal range levels.

Amino Acids

Set forth below is a table indicating the various amino acids which are preferably incorporated within the regimen, a preferred range of dose of the amino acid, and a particular dosage which may be suitable for an average weight and height male approximately 60 years old. The amino acids are as follows:

| Amino Acid | Preferred Range | Particular Dosage |
| --- | --- | --- |
| L-alanine | 100–300 mg | 180 mg |
| L-arginine | 100–300 mg | 162 mg |
| L-aspartic acid | 200–450 mg | 320 mg |
| Bromelain | 100–200 mg | 150 mg |
| L-cystine | 40–100 mg | 69 mg |
| L-glutamine | 400–700 mg | 555 mg |
| glycine | 100–200 mg | 144 mg |
| L-histidine | 50–200 mg | 123 mg |
| L-isoleucine | 150–300 mg | 213 mg |
| L-leucine | 100–400 mg | 291 mg |
| L-lycine | 100–400 mg | 231 mg |
| L-methionine | 100–200 mg | 75 mg |
| pancreatin 4X | 40–150 mg | 75 mg |
| papain NF | 100–200 mg | 150 mg |
| L-phenylalanine | 200–400 mg | 264 mg |
| L-proline | 150–350 mg | 246 mg |
| L-serine | 150–350 mg | 213 mg |
| L-threonine | 100–300 mg | 177 mg |
| L-tyrosine | 200–400 mg | 309 mg |
| taurine | 200–400 mg | 270 mg |
| L-valine | 200–400 mg | 291 mg |

All of the above amino acids are preferably contained within a multi-amino acid capsule, with the dose indicated taken 3 times per day. These are normal ranges, although variation above and below the amount given up to approximately 35% would be appropriate when taking into account the particular condition and characteristics of the patient.

The regimen of the present invention also preferably includes additional doses of amino acid, as follows:

| Amino Acid | Dosage Range | Particular Dosage |
| --- | --- | --- |
| L-arginine | 3,000–5,000 mg | 4,500 mg |
| L-glutamine | 2,000–4,000 mg | 3,000 mg |
| L-tyrosine | 1,000–2,000 mg | 1,500 mg |
| glutathione | 1,000–3,000 mg | 1,500 mg |
| taurine | 4,000–8,000 mg | 6,000 mg |
| ornithine | 3,000–8,000 mg | 6,000 mg |

These additional doses are the amounts to be given during a day, with variation according to the particulars of the patient allowing for up to 35% each way. The dosages given above for the additional amino acids to be given are the total amounts to be taken in a day, so that each dose indicated would be divided approximately into three portions each taken three times per day.

Other amino acids also preferably form part of the regimen. N-acetyl-L-cystine may be administered in doses between 2,000 mg and 4,000 mg per day in total, preferably at around 3,000 mg. This total dosage may be divided into three equal parts, with a variation of about 35% in the dosage range.

Other amino acids which may form part of the regimen include L-carnitine, of which between about 1,000 mg and 2,000 mg preferably forms the total daily dosage divided into three equal portions. Once more, a variation of about 35% or more on the doses may be appropriate according to the patient. Eiycosapentaenoeic acid in the amount of 400 mg–700 mg per day, with a preferred dosage of 540 mg, may be given, while docosahexaenoic acid may also be provided in ranges of 250 mg–450 mg per day, preferably at around 300 mg.

In addition, doses of the following amino acids may be provided: linolenic acid at about 1,125 mg per day; gamma-linolenic acid at about 1,125 mg per day; gamma-linolenic acid at about 687 mg per day; oleic acid at about 570 mg per day; palmitic acid at about 342 mg per day; stearic acid at about 123 mg per day; and palmitoleic acid at about 12 mg per day. All of the above may vary by up to 50%, taking into account the exigencies of the patient. Linolenic acid, an omega-6 essential fatty acid, has been found to be most important for proper prostaglandin formation. These are necessary for the function of the cardiovascular, immune, muscular and nervous systems.

Flax seed oil is preferably administered in the amount of about 3,000 mg per day, divided into three separate doses of about 1,000 mg each. Flax seed oil contains omega-3 and omega-6 essential fatty acids, and a mixture of both animal and grain-based omega-3 and omega-6 fatty acids are used. Flax seed oil assists in the production of prostaglandins which dictate, on a biochemical level, the instructions for reduction of and return to proper levels of blood cholesterol and blood triglyceride levels. Further, they assist and support in immunology system functions. Dosages may be decreased or increased by up to 35%, according to the patient.

The regimen includes administering lipoic acid in the amount of 150 mg per day, with normal range variations being up to 50% or more. Lipoic acid is most important for the production of energy. It is also most important as a metabolic antioxidant. It helps convert calories into useful energy, and directs such calories away from fat production and storage. Lipoic acid also assists in normalizing blood sugar levels and reduces glycation, which is the damage resulting from sugar to critical body components. This damage may lead to accelerated aging, heart disease, and has a profound negative effect when the patient suffers from diabetes.

Other contents of the regimen not falling directly into any specific class include garlic, preferably administered in the amount of about 1,200 mg per day but with normal ranges varying 35% or more above or below this amount. The garlic should include allicin in the approximate amount of 10,000 mcg per gram, once more, with the variations of 35% or more, depending on the patient. Garlic inhibits the enzymes involved in the synthesis of cholesterol in the liver. It also reduces triglycerides, a type of fat stored in the body by decreasing fat absorption. Allicin and ajoene are two of the major constituents of garlic and have a powerful action which support the body's immune system to fight off bacteria and diseases. Garlic helps and assists the patient to have more normal and healthy blood pressure levels and lower cholesterol levels.

EXAMPLES

Patient A

Patient A has been treated by the regimen of the invention for severe cardiovascular disease which almost claimed his life during November and December 1996. Patient A had been on the regimen format and had shown significant recovery. Improvement was almost immediate, i.e. within 48 hours. The patient is now able to ride a bike 6 miles per day. The patient, now approximately 60 years old, had been receiving conventional medical treatment for cardiovascular disease without any significant effect. The patient has gone from NYHA (New York Heart Association) level 4 to level 0.

In FIG. 1 hereof there is shown a Table setting forth the regimen prescribed and administered to Patient A and which resulted in the significant health improvement. As will be noted, the regimen included hormones, amino acids, enzymes, (including coenzymes, antioxidants, vitamins and the like) as well as minerals, mineral ions and garlic, using the various dosages described above. The regimen attempts to optimize biochemistry on the cellular level by providing proper ratios and proportions of the various components normally present in a healthy body so that the effect of each is enhanced in a symbiotic manner.

Patient B

The patient was suffering form arthritis, and responded in a substantial and immediate to the regimen of the invention. The arthritis caused pain to the extent that the patient had to carry her left elbow with her right hand. The patient has had arthritis for about 10 years, starting in the lower spine, and then moving onto the hands and elbows.

Patient B is being treated with a standard regimen, and in addition increased amounts of pregnenolone, chrondroitin, sulfate, glucosan, glucosomine sulfate and melatonin levels. Noticeable signs of recovery and improvement were prompt, and within 48 to 72 hours of first ingesting the regimen, reductions in pain level and swelling in the elbow were evident.

Patient C

This patient is an 82 year old male approximately 70 kilograms, with diabetes and anginal pain on exertion with associated shortness of breath. Over the last 10 years the patient has become dependent on doses of 20–40 units per day of an insulin blend.

Administration of the regimen of the present invention showed certain distinct improvements including: NYHA classification status from between 2 and 3 to between 1 and 2; and a reduction in blood pressure from 140/110 to 130/90.

Patient D

This patient is 39 years old, 5 foot, 11 inches in height, 195 pounds in weight with chronic high pulse rate. At testing, the patient was taking Vitamin C, Vitamin E and beta-carotene. While blood pressure range was fairly normal, pulse was between 95 and 103, increasing significantly when exercising on a stair machine. During exercise, the pulse increased to a 170 BPM (beats per minute) maintained during the entire exercise duration of 20 to 30 minutes. After exercising the pulse rate would return to the earlier range of 95 to 100 BPM.

The patient received 100 mg of garlic, with 10,000 mcg of allicin per gram, 400 mg of niacin (inositol hexanicotonate) and 1,195 mg of potassium gluconate. Within about 1 hour, the pulse rate had dropped to about 84 BPM. 3.5 hours after ingestion, the pulse rate had reduced to 78 BPM, a reduction of more than 25 BPM over a 3.5 hour period.

The following day, the patient's higher pulse rate had returned to between 95–105 BPM. The patient was readministered with doses of 800 mg of garlic, 800 mg of niacin and 1,190 mg of potassium gluconate. Upon once more exercising, the pulse rate was 30–35 BPM less than before using the regimen set forth above. Pulse had dropped from a normal of 170 BPM to a range of 135–140 BPM during exercise, a 20% drop from the previous day when no medication was taken.

Patient E

This patient is an 86 year old male approximately 63 kilograms in weight. Patient has experienced progressive cardiac failure, is bedridden and is unable to move without being breathless. Patient NYHA classification status was 4. Further, signs of cardiac failure were present.

The patient started the regimen of the invention and was followed up approximately one month later. The NYHA status had been reduced to between 2 and 3, while evidence of cardiac failure had disappeared. Previous evidence of edema was absent. The pulse rates had reduced from 120

BPM to about 60 BPM, and blood pressure was at a normal 120/80 about 60 days after the regimen commenced. The patient was able to be partially active, was able to move and carry out body functions independently, and was sufficiently mobile to go out of his house on day-to-day activities. Cardiac function had improved considerably.

FIGS. 2–8 show the advantageous effects of the regimen on up to 23 patients, measuring various parameters.

In FIG. 2, results of a cardiovascular clinical trial are shown, indicating the NYHA status at the start, and the NYHA status 6 months after the regimen commenced. There is an overall significant improvement in the NYHA status of most of the patients.

Figure 3:
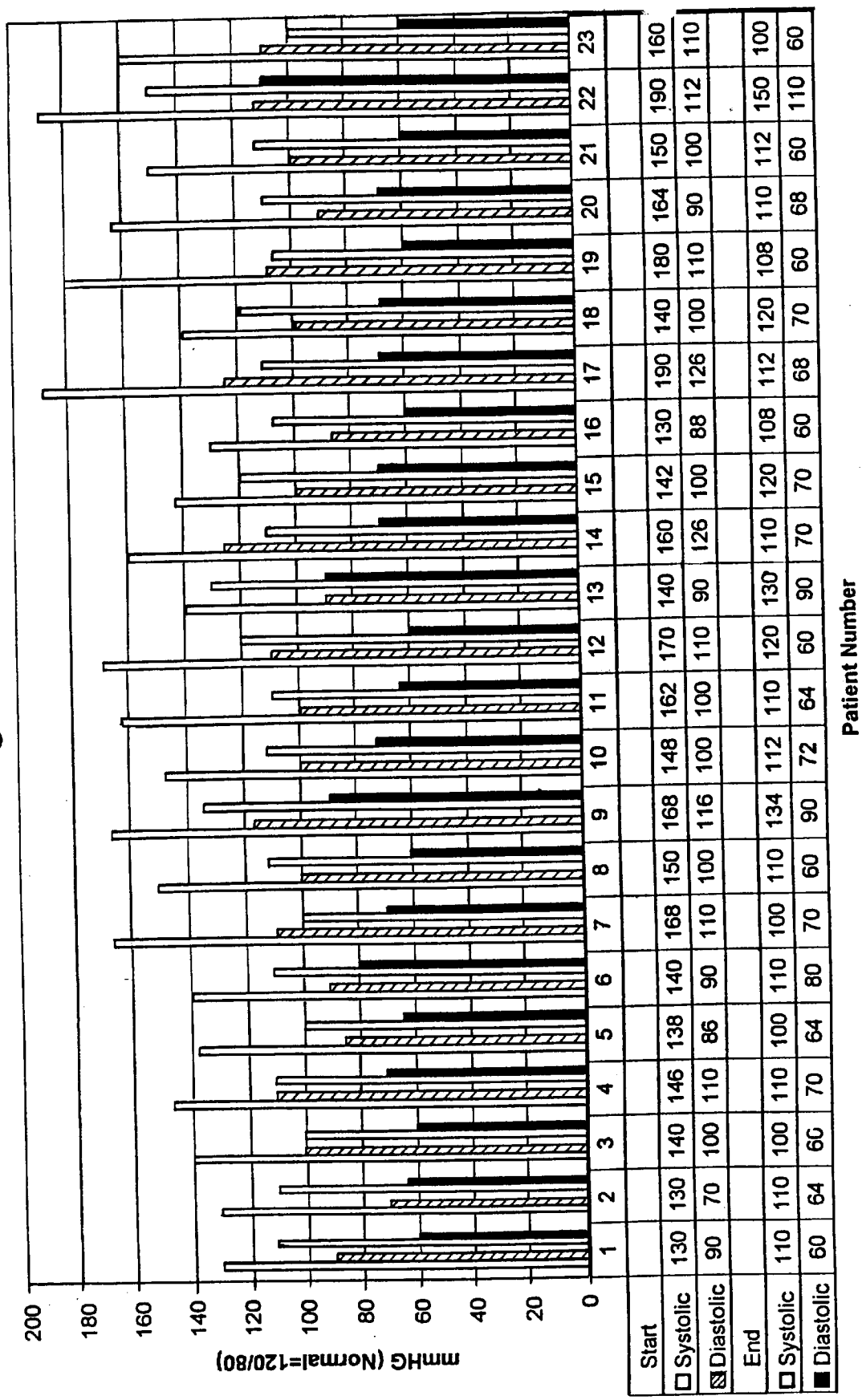
FIG. 3 is a diagram showing start and end blood pressures for the patients.

FIG. 3 shows changes in blood pressure at the start, and 6 months into the treatment, and, once more, improvements, often substantial, are indicated.

Figure 4:
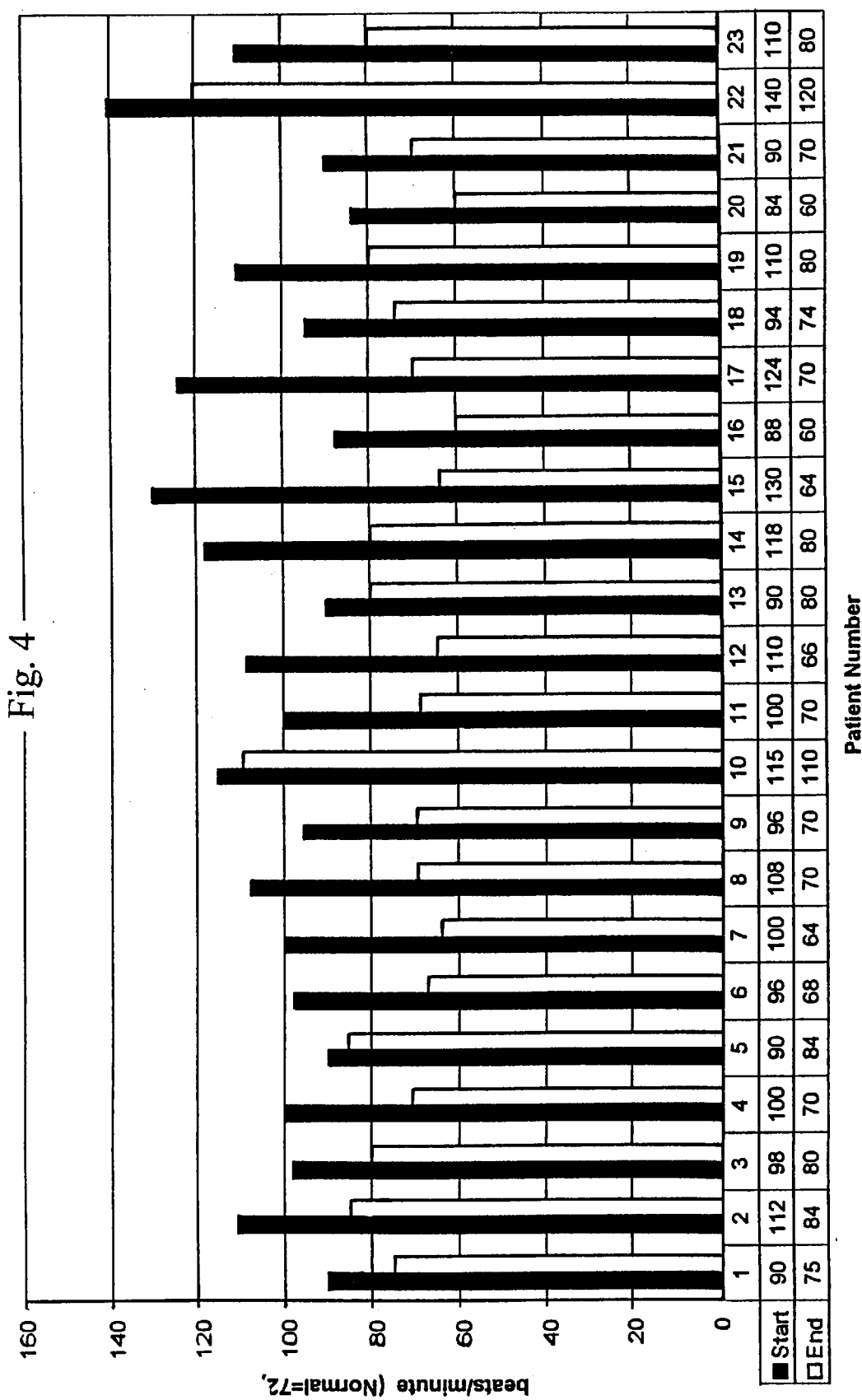
FIG. 4 is a diagram showing start and end pulse rates for the patients.

FIG. 4 is a graph showing Pulse at the start of the program and 6 months into the regimen. Once more, significant reductions in pulse rate measured in 'beats per minute' are shown for those patients on the regimen.

Figure 5:
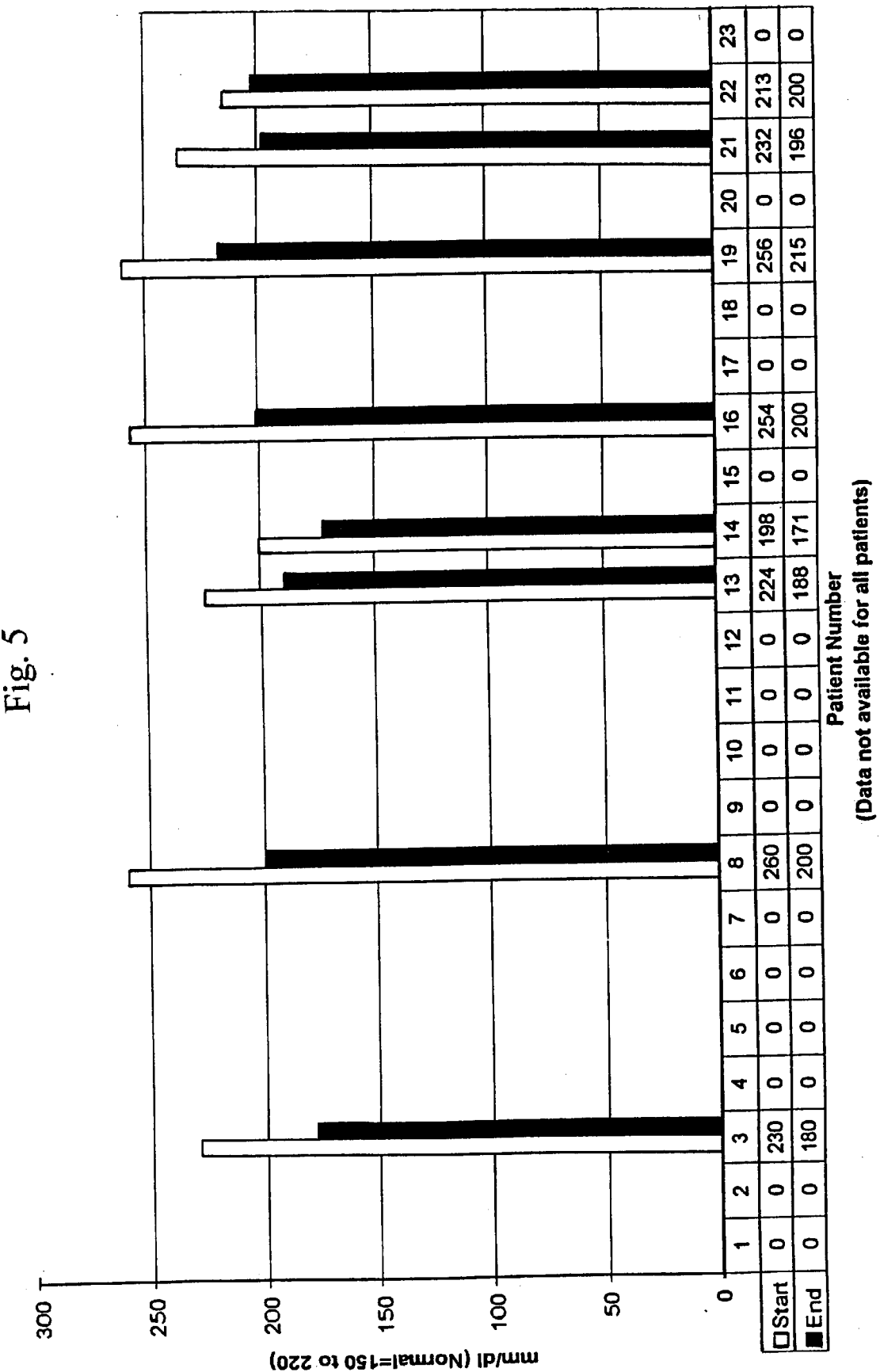
FIG. 5 is a diagram showing start and end total cholesterol for selected patients.
Figure 6:
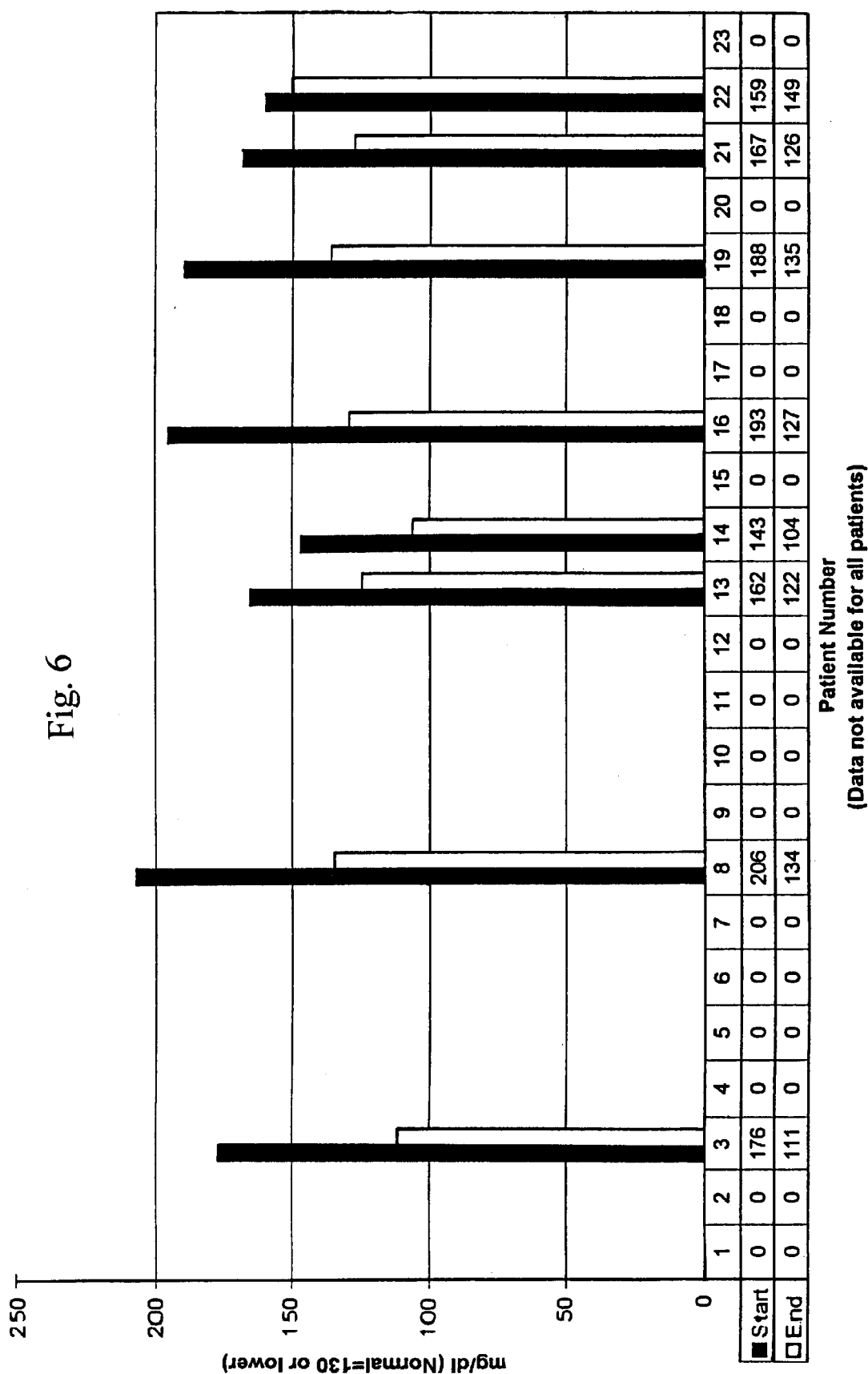
FIG. 6 is a diagram showing start and end LDL cholesterol levels for selected patients.
Figure 7:
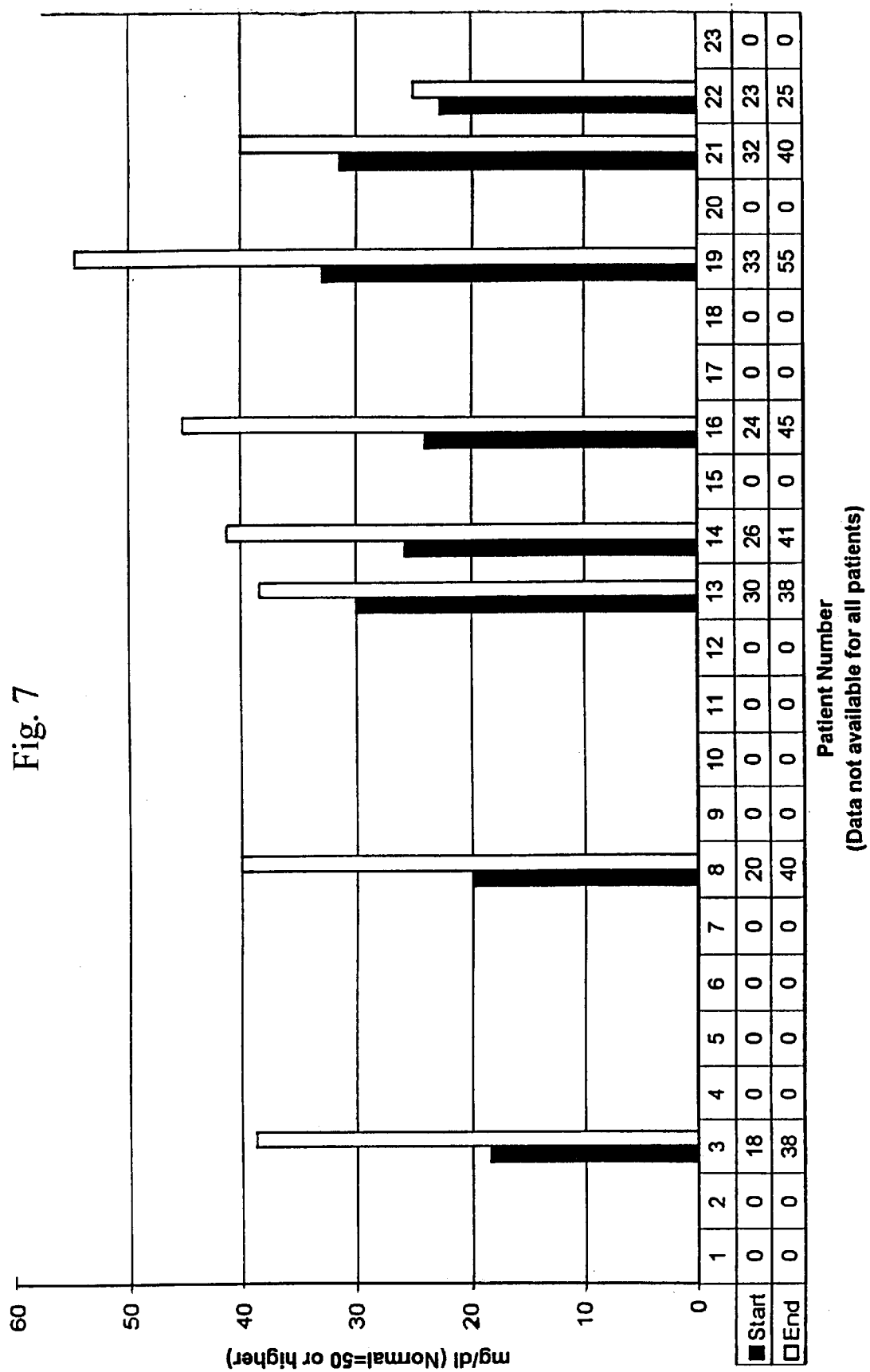
FIG. 7 is a diagram showing start and end HDL cholesterol levels for selected patients.

FIG. 5 shows total cholesterol measured in certain patients at start and 6 months into the regimen. Reductions in cholesterol levels are indicated. In FIG. 6, a table showing the same patients as indicated in the previous Figure illustrating the LDL cholesterol changes shown between start and 6 months, while in FIG. 7 a similar table indicates the changes in HDL cholesterol.

Figure 8:
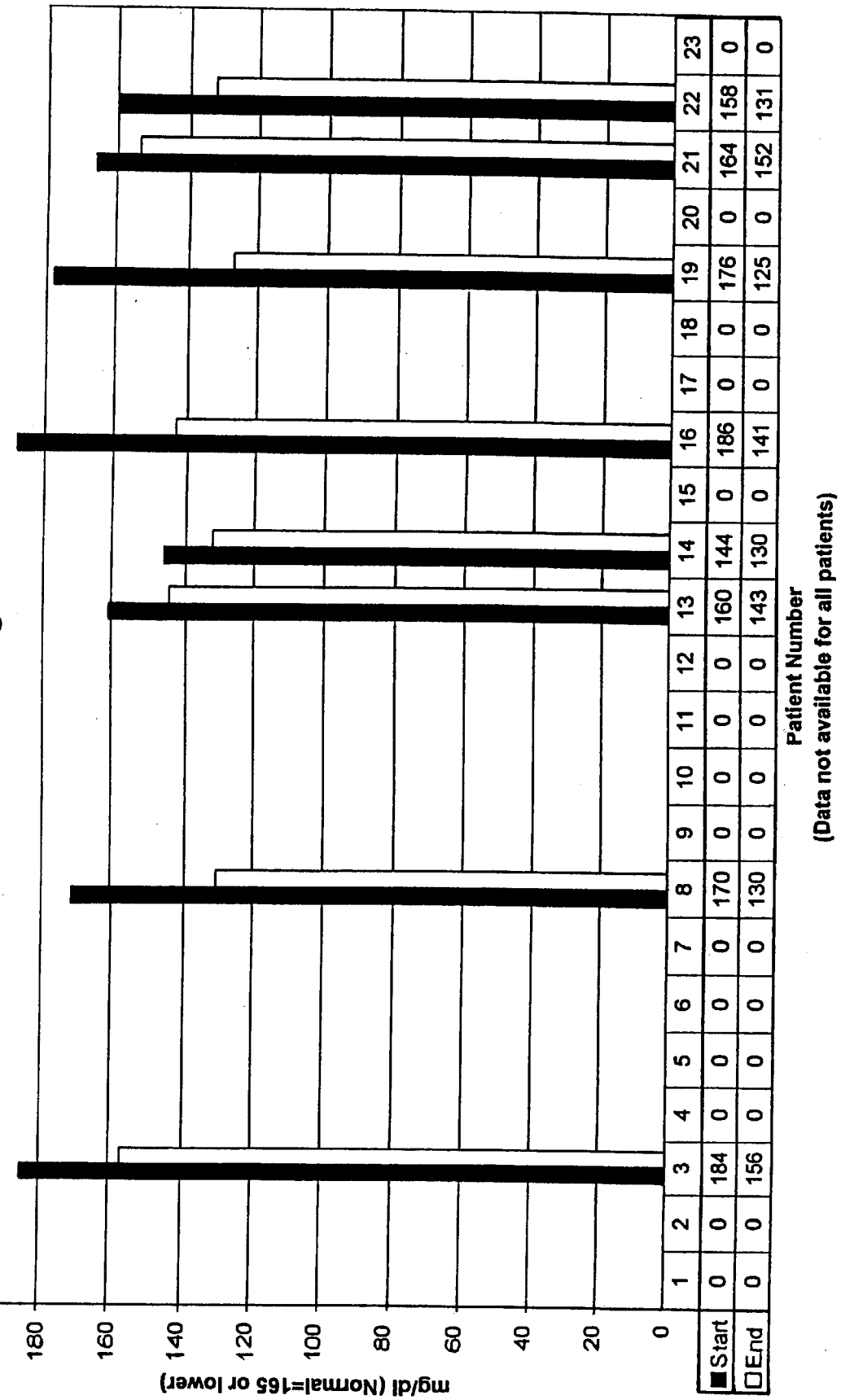
FIG. 8 is a diagram showing start and end triglyceride levels for selected patients.

Finally, in FIG. 8, the change in triglycerides was measured between start and 6 months into the regimen, and reduction in triglyceride levels was shown in all of the patients.

The composition or biochemical formula which is the regimen of the invention constitutes a totally pervasive attack against a disease, and attempts to overwhelm the disease within the body from many different angles, pathways, approaches and the like. The approach is to change the sick body patient biochemistry quickly and massively and where possible, restore various biochemical levels, on a wide platform basis, to those seen in an earlier time period of the person's life. During that earlier time, the body was far better able to fight disease and create a medium where many diseases found it difficult to survive.

The regimen described in this application is hormonal, amino acid and enzyme driven. By taking an overall and complete approach to the restoring of biochemical balance, the regimen initiates inside the cells instructions to increase the rate of biochemical reaction. This had a positive response for the health of the patient, and a negative outcome for the disease being combatted. By regulating the DNA and RNA by hormonal commands, and copying the cellular language instructions of the body earlier in the biological life cycle, molecular, cellular and tissue enhancement, regeneration and total improvement can be achieved. The regimen attempts to reverse the existing cellular operational code, providing a different direction.

I claim:

1. A composition for use by humans, the composition comprising a combination of:
   (a) at least one hormone selected from the group consisting of at least 100–125 mg dehydroepiandrosterone (DHEA), and at least 5 mg of melatonin;
   (b) at least one amino acid selected from the group consisting of taurine, arginine, tyrosine and glutamine;
   (c) at least one enzyme comprising 240–600 mg coenzyme $Q_{10}$; and
   (d) at least one mineral selected from the group consisting of calcium, magnesium, potassium, zinc and copper;

the hormone, amino acid, enzyme and mineral in the combination operating synergistically to provide both nutrients and regulatory components.

2. A composition as claimed in claim 1 wherein DHEA is present so as to provide a dose of up to 200 mg per day.

3. A composition as claimed in claim 1 wherein melatonin is present so as to provide a dose of 5–12 mg per day.

4. A composition as claimed in claim 1 wherein coenzyme Q10 is present in the composition so as to provide a dose of between 360 mg and 540 mg per day.

5. A composition as claimed in claim 1 further comprising an antioxidant.

6. A composition as claimed in claim 5 wherein the antioxidant is selected from one or more of the group consisting of: multi-carotenes, alpha-, beta- and gamma carotenes, lycopene, lutein zeanthins, Vitamin E, Vitamin C and Niacin.

7. A composition as claimed in claim 6 wherein alpha-carotene is dosed at 25–40 mg per day, beta-carotene is dosed at 50–60 mg per day and gamma-carotene is dosed at 1–5 mg per day.

8. A composition as claimed in claim 6 wherein lycopene is dosed at 1–5 mg per day, lutein is dosed at 1–10 mg per day and zeanthin is dosed at 200–500 mcg per day.

9. A composition as claimed in claim 6 wherein Vitamin E is dosed at 800–4000 IU per day.

10. A composition as claimed in claim 9 wherein Vitamin E is dosed at between 2000 and 3000 IU per day.

11. A composition as claimed in claim 6 wherein Vitamin C is dosed at between 1500 and 4000 mg per day.

12. A composition as claimed in claim 6 wherein the Niacin contains inositol hexanicotinate.

13. A composition as claimed in claim 12 wherein Niacin inositol hexanicotinate is dosed at between 400 and 600 mg per day.

14. A composition as claimed in claim 12 wherein the Niacin inositol hexanicotinate is dosed at between 800 and 1200 mg per day.

15. A composition as claimed in claim 1 comprising a Vitamin B-complex, the Vitamin B-complex containing one or more of the components in the following group: folic acid, Vitamin B1, Vitamin B2, Vitamin B3 (niacin), Vitamin B3 (niacinamide), Vitamin B5, Vitamin B6, Vitamin B12, biotin, inositol, choline and para-aminobenzoic acid (PABA).

16. A composition as claimed in claim 15 wherein the Vitamin B-complex contains all of said components.

17. A composition as claimed in claim 15 wherein the Vitamin B-complex comprises the following components dosed per day in the range indicated:

| Component | Range (per day) |
| --- | --- |
| Folic Acid | 2400 mcg–4800 mcg |
| Vitamin B1 | 100 mg–200 mg |
| Vitamin B2 | 100 mg–200 mg |
| Vitamin B3 (niacin) | 10 mg–30 mg |
| Vitamin B3 (niacinamide) | 100 mg–300 mg |
| Vitamin B5 | 100 mg–400 mg |
| Vitamin B6 | 150 mg–350 mg |
| Vitamin B12 | 100 mcg–200 mcg |
| Biotin | 600 mcg–1,200 mcg |
| Inositol | 100 mg–200 mg |
| Choline | 100 mg–200 mg |
| PABA | 100 mg–200 mg. |

18. A composition as claimed in claim 1 further comprising one or more of the group consisting of: calcium, magnesium, Vitamin D3, iodine, iron, potassium gluconate, zinc, Vitamin K, copper, chromium, lecithin, lecithin choline, selenium and piperine.

19. A composition as claimed in claim 18 wherein calcium is present in the composition so as to be dosed at between 1500 and 2500 mg per day.

20. A composition as claimed in claim 18 wherein magnesium is present in the composition so as to be dosed at between 600 and 1000 mg per day.

21. A composition as claimed in claim 18 wherein potassium gluconate is present in the composition so as to be dosed at between 1800 and 5400 per day, the potassium gluconate having about 300 to 900 mg of potassium.

22. A composition as claimed in claim 18 wherein zinc is present in the composition so as to be dosed at between 60 and 120 mg per day.

23. A composition as claimed in claim 18 wherein vitamin K is present in the composition so as to be dosed at between 600 and 1200 mcg per day.

24. A composition as claimed in claim 18 wherein copper is present in the composition so as to be dosed at between 2 and 8 mg per day, the copper being linked to an amino acid.

25. A composition as claimed in claim 18 wherein lecithin choline is present in the composition so as to be dosed at between 3600 and 7200 mg per day, 25% to 50% whereof comprises phosphatidylcholine.

26. A composition as claimed in claim 18 wherein chromium is present in the composition as a chromium piconolate complex and is dosed at between 1200 and 2000 mcg per day.

27. A composition as claimed in claim 18 wherein selenium and piperine comprise a mixture in an approximately 10:1 ratio respectively, the mixture having about 300 to 600 mcg selenium and 45 to 100 mcg piperine dosed daily.

28. A composition as claimed in claim 1 wherein the amino acid is selected from one or more of the group consisting of the following, and being present in the amount indicated dosed per day:

| Amino Acid | Range (per day) |
| --- | --- |
| L-alanine | 100–300 mg |
| L-arginine | 100–300 mg |
| L-aspartic acid | 200–450 mg |
| Bromelain | 100–200 mg |
| L-cystine | 40–100 mg |
| L-glutamine | 400–700 mg |
| glycine | 100–200 mg |
| L-histidine | 50–200 mg |
| L-isoleucine | 150–300 mg |
| L-leucine | 100–400 mg |
| L-lycine | 100–400 mg |
| L-methionine | 100–200 mg |
| pancreatin 4X | 40–150 mg |
| papain NF | 100–200 mg |
| L-phenylalanine | 200–400 mg |
| L-proline | 150–350 mg |
| L-serine | 150–350 mg |
| L-threonine | 100–300 mg |
| L-tyrosine | 200–400 mg |
| taurine | 200–400 mg |
| L-valine | 200–400 mg. |

29. A composition as claimed in claim 28 wherein additional quantities of one or more amino acids selected from the following group, and being present in the amount indicated dosed per day, are present in the composition:

| Amino Acid | Dosage Range |
| --- | --- |
| L-arginine | 3,000–5,000 mg |
| L-glutamine | 2,000–4,000 mg |
| L-tyrosine | 1,000–2,000 mg |
| glutathione | 1,000–3,000 mg |
| taurine | 4,000–8,000 mg |
| ornithine | 3,000–8,000 mg. |

30. A composition as claimed in 28 further comprising one or more compounds selected from the group consisting of: N-acetyl-L-cystine, L-carnitine, eiycosapentaenoeic acid, linoloic acid, gamma-linoloic acid, docosahexaenoic acid, oieic acid, palmitic acid, stearic acid, and palmitoleic acid.

31. A composition as claimed in claim 1 further comprising flax seed oil present in the composition so as to be dosed at about 3000 mg per day.

32. A composition as claimed in claim 1 further comprising lipoic acid present in the composition so as to be dosed at about 75 to 225 mg per day.

33. A composition as claimed in claim 1 further comprising garlic present in the composition so as to be dosed at about 750 mg to 1700 mg per day.

34. A method of forming a composition for use by a human body, the method comprising:

providing in combination: (a) at least one hormone selected from the group consisting of at least 100–125 mg dehydroepiandrosterone (DHEA) and at least 5 mg of melatonin; (b) at least one amino acid selected from the group consisting of taurine, arginine, tyrosine and glutamine; (c) at least one enzyme comprising about 240–600 mg coenzyme $Q_{10}$; and (d) at least one mineral selected from the group consisting of calcium, magnesium, potassium, zinc and copper; and adjusting the relevant amounts of said hormone, amino acid, enzyme and mineral in the combination so that the combination operates synergistically to provide both nutrients and regulatory components to the body.

* * * * *